US012569275B2

(12) United States Patent
Regensburger

(10) Patent No.: US 12,569,275 B2
(45) Date of Patent: Mar. 10, 2026

(54) MEDICAL INTERVENTION DEVICE, COMPUTER-IMPLEMENTED METHOD FOR ASCERTAINING AND OUTPUTTING A POSITIONING INSTRUCTION AND COMPUTER PROGRAM

(71) Applicant: Siemens Healthineers AG, Forchheim (DE)

(72) Inventor: Alois Regensburger, Poxdorf (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/756,302

(22) Filed: Jun. 27, 2024

(65) Prior Publication Data

US 2025/0000544 A1     Jan. 2, 2025

(30) Foreign Application Priority Data

Jun. 29, 2023    (EP) .................................... 23182397

(51) Int. Cl.
　　*A61B 17/34*　　　(2006.01)
　　*A61B 34/10*　　　(2016.01)
　　*A61B 34/20*　　　(2016.01)
(52) U.S. Cl.
　　CPC .......... *A61B 17/3403* (2013.01); *A61B 34/10* (2016.02); *A61B 34/20* (2016.02); *A61B 2034/107* (2016.02); *A61B 2034/2055* (2016.02)
(58) Field of Classification Search
　　CPC ..... A61B 17/3403; A61B 34/10; A61B 34/20; A61B 2034/107; A61B 2034/2055
　　See application file for complete search history.

(56) References Cited

U.S. PATENT DOCUMENTS 7,876,942 B2 *　1/2011　Gilboa ..................... A61B 6/12
　　　　　　　　　　　　　　　　　　　　　　　382/128
10,183,180 B2 *　1/2019　Brosens-Kessels .........................
　　　　　　　　　　　　　　　　　　　　　　　A61N 5/1071
(Continued)

FOREIGN PATENT DOCUMENTS

CN　　　104039260 A　*　9/2014　............. A61B 34/20
DE　102019211870 A1　　9/2020
(Continued)

OTHER PUBLICATIONS

Improved Laser Needle Guidance; Dr. Alois Regensburger et al., Siemens AG 2019. pp. 1-3.
(Continued)

*Primary Examiner* — Tan-Uyen T Ho
*Assistant Examiner* — Cherie M Poland
(74) *Attorney, Agent, or Firm* — Lempia Summerfield Katz LLC

(57) ABSTRACT

A medical intervention device including a bendable medical instrument, which may be inserted into an intervention area of an examination object and has a proximal portion for handling, an alignment element on the instrument, having a projection surface with a marking, a representation facility, light-guiding facility, and a processing facility, having: an evaluation unit configured to ascertain a predictive continuation trajectory from image data representing the intervention area and positioning data describing the current position and location of the instrument using property data describing the bendability of the instrument, and an output unit for outputting a representation of the intervention area and the predictive continuation trajectory based on the image data on the representation facility. The light-guiding facility is configured for projecting a light pattern onto the projection surface in such a way that a positioning instruction for position correction is produced at the proximal portion of the (Continued)

instrument in order to achieve the at least one predictive continuation trajectory upon further insertion of the instrument.

15 Claims, 9 Drawing Sheets

(56)                    References Cited

U.S. PATENT DOCUMENTS

| 10,842,409 | B2 * | 11/2020 | Hendriks | .............. G06T 7/0012 |
| 11,298,150 | B2 | 4/2022 | Regensburger | |
| 11,622,699 | B2 * | 4/2023 | Sela | ....................... A61B 5/065 |
| | | | | 600/417 |
| 2008/0208041 | A1 | 8/2008 | Gilboa | |
| 2014/0357898 | A1 * | 12/2014 | Kawano | ................. C08G 61/02 |
| | | | | 570/183 |
| 2014/0357989 | A1 | 12/2014 | Hendriks et al. | |
| 2015/0150591 | A1 | 6/2015 | Takagi | |
| 2016/0184611 | A1 * | 6/2016 | Brosens-Kessels | ......................... |
| | | | | A61N 5/1001 |
| | | | | 600/7 |
| 2020/0315711 | A1 | 10/2020 | Richter | |
| 2022/0167868 | A1 * | 6/2022 | Sela | ....................... A61B 34/20 |
| 2022/0331059 | A1 | 10/2022 | Galili | |
| 2024/0050184 | A1 * | 2/2024 | Zeng | ....................... A61B 90/11 |

FOREIGN PATENT DOCUMENTS

| WO | WO-2021066752 A1 * | 4/2021 | ......... A61B 17/3403 |
| WO | 2022113085 A1 | 6/2022 | |
| WO | 2022254436 A1 | 12/2022 | |

OTHER PUBLICATIONS

European Intention to Grant for Application No. 23182397.2-1122 dated Mar. 4, 2025, with English translation.
European Search Report for Application No. 23182397.2-1122 dated Dec. 15, 2023, with English translation.

* cited by examiner

MEDICAL INTERVENTION DEVICE, COMPUTER-IMPLEMENTED METHOD FOR ASCERTAINING AND OUTPUTTING A POSITIONING INSTRUCTION AND COMPUTER PROGRAM

CROSS REFERENCE TO RELATED APPLICATIONS

This application claims the benefit of EP 23182397.2 filed on Jun. 29, 2023, which is hereby incorporated by reference in its entirety.

FIELD

Embodiments relate to a medical intervention device including an elongate medical instrument that may be partially inserted into an intervention area of an examination object for an intervention, has a proximal portion to be arranged outside the examination object for manual handling of the medical instrument and is at least partially bendable.

BACKGROUND

Elongate medical instruments that are inserted into a patient for examination and/or treatment of the patient are known. Here, for example needles may be mentioned as medical instruments, for example biopsy needles, ablation needles and the like. Here, it is usually provided that the needle is moved within an examination object in such a way that its tip reaches a target area, for example a target object, within the examination object. The target area may, for example, be a tumor or other tissue of interest or tissue to be treated. In order to reach the target area reliably, for example to support a user guiding the instrument manually, it is necessary to take account of a large number of effects.

For example, it may be noted that when an instrument, for example a needle, is inserted into soft tissue, the soft tissue typically does not remain static. Movements take place in the examination object, for example macroscopic movements of a patient and/or cyclical movements, such as respiratory movements and heartbeat. The instrument itself may also lead to tissue displacement. For example, organs and/or other anatomical structures may be pushed to the side and/or backward and/or other deformations may occur. Consequently users, for example interventional radiologists, often dispense with navigation during needle guidance and guide the needle (or another instrument) forward step by step, interrupted by repeated imaging, for example X-ray imaging, and path correction. Here, it is, for example, known to move the proximal portion of the instrument, i.e., the portion pointing toward the user, that has already been partially inserted, sideways to correct the instrument path and then to further advance the instrument a little. If the path of the instrument deviates too much from the intended path, the instrument may be pulled back a little and corrected again. These corrections to the instrument path are based on the user's intuition and experience, wherein each correction to the instrument path affects the tissue of the examination object, prolongs the duration of the intervention and increases radiation exposure due to repeated image capturing by X-ray imaging.

Depending upon the diameter, material, and flexibility of the instrument, i.e., the mechanical properties, the lateral movement of the proximal portion of the instrument leads either to a rigid change in direction of the already partially inserted instrument within the anatomy or to elastic bending of the instrument, thus enabling curved needle paths. There is also a wide transition range in which both a change of direction and bending occur. To date, all these estimates have been left to the experience and intuition of the user.

The most common procedure used today for interventions with medical instruments, for example needles, is the so-called "step-and-shoot method", as already explained above. Here, the needle is advanced step by step and a position check is performed regularly using X-ray imaging, wherein, whenever the needle does not lead to the target area in the current direction, it is realigned appropriately. It is then advanced again a little further and a new control scan is performed. However, this requires the user to have extensive experience.

The prior art has also proposed that advance planning be performed in which a static and linear needle trajectory is planned, for example in a three-dimensional preliminary image dataset of the examination object. This planned needle trajectory may be visualized to perform the intervention by optical navigation, wherein, for example, crossed laser lines may indicate the needle trajectory. However, this procedure does not provide for adaptation to the possible changes to the anatomy or take account of bendability of the instrument, for example the needle.

The prior art has also proposed that the instrument, for example the needle, be inserted by a robot. A robot advances a needle step by step and a control scan is executed by computed tomography. This determines the current position and shape and possibly the current location of the target area within the anatomy in the image data from which an adapted needle path including correct bending of the portion outside the patient is automatically calculated. The robot is then actuated according to the adapted needle path. When these steps have been executed several times, the needle automatically reaches the target area by a bend adapted to the change in the anatomy. For example, WO 2022/254436 A1 discloses systems, devices and methods for real-time updating of a trajectory for inserting a medical instrument to a target in a body of a subject, wherein closed-loop control toward the moving target takes place.

For the use of rigid screws, a user may be supported by the generation of a representation that uses overlaying of image data to indicate where the screw would move if it were advanced further straight ahead into the examination object.

BRIEF SUMMARY AND DESCRIPTION

The scope of the present disclosure is defined solely by the claims and is not affected to any degree by the statements within this summary. The present embodiments may obviate one or more of the drawbacks or limitations in the related art. Independent of the grammatical term usage, individuals with male, female or other gender identities are included within the term.

Embodiments provide a user with intuitive assistance when manually advancing medical instruments in an examination object, that for example enables the target area to be reached quickly and reliably.

Embodiments are explained in more detail below with reference to a medical intervention device, a method, and a computer program. Embodiments and explanations relating to the medical intervention device may also be transferred to the computer-implemented method and vice versa.

In an embodiment, a medical intervention device includes: an elongate medical instrument, that may be partially inserted into an intervention area of an examination object for an intervention, has a proximal portion to be arranged outside the examination object for manual handling of the medical instrument and is at least partially bendable, for example elastically bendable, an alignment element arranged on the instrument and/or integrated therein, that has a projection surface with at least one marking that marks at least one point, a representation facility, a processing facility that has: an evaluation unit that is configured to ascertain at least one predictive, for example non-linear, continuation trajectory from image data representing the intervention area of the examination object and positioning data describing the current position and location of the medical instrument using property data describing the bendability of the medical instrument, and an output unit for outputting a representation of the intervention area and the at least one continuation trajectory based on the image data on the representation facility; and a light-guiding facility for projecting at least one light pattern onto the projection surface in such a way that a combined view of at least one of the least one marking and the light pattern produces a positioning instruction for manual position correction at the proximal portion of the medical instrument in order to achieve one to be selected of the at least one continuation trajectory upon further insertion of the medical instrument.

The examination object may, for example, be a human and/or veterinary patient and/or an examination phantom. A medical intervention device, that may also be understood as a medical intervention system, therefore has a plurality of components that interact to allow the output of intuitive supportive positioning instructions.

The medical instrument is for example a surgical instrument, for example a needle, for example a puncture needle. Other medical instruments include drills, screws, diagnostic instruments, such as, for example, endoscopes and/or catheters, and/or trocars. The medical instrument is elongate, i.e., elongated, and preferably needle-shaped and/or rod-shaped. In the operating state of the device, the medical instrument may be at least partially arranged within the examination object, specifically in the intervention area. In the present case, the portion of the medical instrument arranged within the examination object is also referred to as the distal portion.

The alignment element may be arranged in a defined locational relationship, for example in a defined relative spatial position and/or relative alignment and/or relative pose, on the medical instrument, for example the proximal section of the medical instrument. The alignment element and/or the medical instrument may have a fastening element, for example a clamping device and/or a plug-in device and/or a magnetic holder. Alternatively, or additionally, the alignment element may be at least partially integrated into the medical instrument, for example at the proximal portion, for example on a surface of the medical instrument.

The alignment element includes a projection surface on which at least one marking is provided. Apart from the marking, the projection surface may for example be colored in a specific color, for example white. The projection surface is for example formed by at least part of the visible surface of the alignment element. The at least one marking marks at least one point and may be at least point-shaped. The at least one marking may be configured as a geometric object, for example as a line and/or a circle and/or a cross. Furthermore, the at least one marking may be configured as a contrast object, for example an imprint, and/or an elevation and/or a recess on a substrate of the alignment element, for example a surface of the alignment element.

The processing facility may include an interface for receiving the image data (and possibly the positioning data). The evaluation unit may be configured to ascertain the positioning data by evaluating the image data, that for example also depicts the medical instrument in the intervention area. However, the positioning data may also be at least partially provided in another way, for example by a position-determining system that ascertains the position and/or orientation of the medical instrument in another way and is registered with the image data.

The processing facility may be configured to receive the medical image data configured via the interface. The reception of the image data may for example include acquiring and/or reading a computer-readable data memory and/or receiving from a data storage unit, for example a database. However, the image data may be provided by a medical imaging facility, that may also be part of the intervention device.

Advantageously, the image data includes a two-dimensionally or three-dimensionally spatially resolved map of the examination object. In addition, the image data may map the examination object in a time-resolved manner. The image data may include a plurality of image points, for example pixels or voxels, with image values, for example intensity values and/or attenuation values, that map, for example represent the examination object. The image data may include X-ray image data of the examination object, for example a computed tomography image dataset and/or projection images, for example fluoroscopy images. The image data may also at least partially map the medical instrument.

The representation facility may include a screen and/or a monitor and/or a projector and/or smart glasses, that are configured to display the graphical representation.

The light-guiding facility may include a light source, for example a laser light source, that is configured to emit the light pattern. For this purpose, the light-guiding facility may, for example, include an optical aperture. As will be explained in more detail below, the processing facility may include an actuating unit for actuating the light-guiding facility. The light-guiding facility may for example be configured to emit at least one laser fan and/or at least one laser beam for projecting a line or a point. The light-guiding facility may include at least one actuator to effect a change in the light pattern. Actuation by the actuating unit may relate to the actuator.

If the examination object is placed on a patient bench that may be adjusted, the relative position and orientation of the light pattern may also be set by actuating an actuator on the patient bench. For example, embodiments are known in which two laser fans, i.e., lines in the light pattern, indicate the location of a captured (usually axial) computed tomography slice and a center of the imaging facility, here a computed tomography facility. The center line may then also be positioned as desired by lateral adjustment of the patient bench.

The processing facility may serve as a control facility of the intervention device. It may have at least one memory and at least one processor. Functional units, such as, for example, the evaluation unit and the output unit, may be formed by hardware and/or software. In addition to the functional units mentioned, obviously further functional units are also conceivable in principle.

The evaluation unit is configured to ascertain continuation trajectories that result from certain position corrections at the proximal portion and further advancement. While the representation allows the user to evaluate the at least one continuation trajectory, the positioning instruction is used to instruct the user to undertake these position corrections for the (selected) trajectory. Taking account of the (current) image data enables the current state of the anatomy of the examination object in the intervention area to be included here. However, it is also not assumed that medical instrument is rigid, but that these mechanical properties that allow bendability are assigned to the actual, for example elastically bendable, instrument when ascertaining the at least one continuation trajectory, so that a reliable and accurate prediction is obtained and, at the same time, the support of the user in manual guidance of the medical instrument, for example the needle, also relates to a property or a degree of freedom that was previously only taken into account intuitively by the user, namely the bendability of the instrument. This may for example enable a three-dimensional assessment during the ascertaining. Herein, the bendability of the instrument is for example not restricted to the proximal portion, but also to the distal portion that is inserted or may be inserted into the patient, so that bent shapes may/may also occur in the patient.

The evaluation unit may be configured to ascertain the at least one continuation trajectory by simulating and/or modeling the impact of a position correction of the medical instrument undertaken in the proximal portion, for example including bending, on the behavior of the instrument at the distal portion within the examination object, for example during advancement. As will be explained in more detail below with regard to the first embodiment, if markings are to be assigned to specific continuation trajectories, the bending in the proximal portion may be specified such that the position correction described by the respective marking is used. Alternatively or additionally, the evaluation unit is provided with an item of target information about an instrument target, for example a target area, in the intervention area and that this is configured to ascertain at least one continuation trajectory for the greatest possible approximation to this instrument target and a position correction required for this purpose (for example including bending of the proximal portion). In the second embodiment, that is described in more detail below, this may then be indicated by a projection point. In the first embodiment mentioned, for example a nearest marking describing this position correction may be ascertained by the evaluation unit. Bending at the proximal portion may also result in bending at the distal portion.

In the representation on the representation facility, the continuation trajectories, that may be understood as virtual continuations, may, for example, be represented as image data overlaid at a precise location. Here, the continuation trajectories may be displayed as graphical elements, for example as a line and/or an arrow. Herein, the continuation trajectories may for example be at least partially non-linear, for example curved.

In this way, the correction of the instrument path is greatly simplified, for example for inexperienced users, and interventions may be performed more time-efficiently and with less use of radiation. For example, in this way, an improved "step-and-shoot" method is provided in which taking account of the bendability of the medical instrument and the associated provision of positioning instructions as workflow instructions provide significant added value.

The method described here may for example be performed without advance planning. This was not possible with previous light pattern-guided interventions with elongate medical instruments, for example needles. The user may insert the medical instrument a first distance into the examination object, initially unguided, possibly also under live imaging, after which image data may be captured. If desired or necessary, the positioning instructions may be used to correct the instrument trajectory accordingly in order to reach the desired target area, i.e., the instrument target. Here, this may also be performed several times during the intervention. Alternatively, it is possible to use a method for instrument navigation known from the prior art, for example laser needle guidance.

Additional embodiments may be used as to how the positioning instruction may be issued to the user in an intuitive and targeted manner by the light pattern and the at least one marking.

In a first embodiment, it may be provided that the light pattern marks a projection point that, in order to select the selected continuation trajectory, is to be brought into congruence with a marking assigned to the selected continuation trajectory. The output unit is configured to generate the representation with marking information assigned to the at least one continuation trajectory and describing the assigned marking. Specifically, it may be provided that, to bring the projection point into congruence with the marking, a target point defined by the marking and the projection point are brought into coincidence. In the case of a plurality of continuation trajectories and a plurality of markings, the markings on the one hand and the marking information on the other may be optically distinguishable. In other words, it may be provided that the markings have an optically distinguishable property. The continuation trajectories may likewise be represented with optically distinguishable properties for outputting the marking information, wherein for example the optically distinguishable property of the continuation trajectories or generally of the marking information with the optically distinguishable property may in each case correspond in pairs to one of the markings. The plurality of markings may, for example, have color coding and/or black-and white coding and/or a surface condition, for example reflectivity and/or a contour, as the optically distinguishable property and the plurality of markings may be uniquely identifiable by the optically distinguishable property. In an embodiment, in the case of color coding of markings, corresponding colors may also be selected for the continuation trajectories in the representation.

The processing facility is aware of the markings, for example the plurality of markings, and their location on the alignment element, so that the evaluation unit may be configured to ascertain the appropriate continuation trajectories in a targeted manner for markings and the resulting position corrections including bending of the medical instrument at the proximal portion, as already explained above.

As will be explained later, if the position correction has not yet been undertaken, the projection point may, for example, be projected along the longitudinal direction of at least the proximal portion of the instrument, for example a shaft axis of an instrument shaft of the instrument. This adjustment may be effected by actuating the light-guiding facility, for example on the basis of the positioning data or on the basis of planning information, by an actuating unit of the processing facility. In other words, the processing facility may have the actuating unit, that is configured to actuate the light-guiding facility for outputting of the light pattern in such a way that the projection point is projected along a current longitudinal direction of at least the proximal portion of the medical instrument, for example along a shaft axis of an instrument shaft. Additionally or alternatively, it may also be provided that the actuating unit is configured to actuate a patient bench on which the examination object is arranged in such a way that the relative position and orientation of the medical instrument and the light pattern is such that the projection point is projected along a current longitudinal direction of at least the proximal portion of the medical instrument, for example along a shaft axis of the instrument shaft. Expediently, here a center point of the alignment element may correspond to the projection point that indicates the current longitudinal direction.

In this embodiment, the alignment element may be understood as a type of "target", wherein, to perform the position correction, the proximal portion of the medical instrument, for example at a specified point of application, is manipulated in such a way that the projection point coincides with a marking corresponding to a selected continuation trajectory. The marking information in the representation indicates which marking this is.

In an embodiment, it may be provided that the light pattern includes at least one orientation line indicating the orientation of the representation, for example an image plane of a slice of the image data used in the representation. For this purpose, the light-guiding facility may be actuated accordingly via the actuating unit and/or registered with a medical imaging facility that provides the image data. For example, in the case of a computed tomography facility in which axial slices are usually reconstructed as slice images, the slice orientation may also be fixed, so that the light-guiding facility may also be configured for fixed projection of the orientation line in such a way that this indicates the slice orientation. Such an orientation line may for example be indicated by a laser fan. Therefore, when using computed tomography facilities, it is also possible to use light-guiding facilities that are already provided and that indicate slice orientation on the patient.

In the case of a correspondingly actuatable light-guiding facility with an adjustable light fan and/or laser fan for the orientation line, when the representation orientation is adapted, it is also possible for the orientation line to be adapted. This is for example expedient if, as is often the case, work is not to be carried out within the same axial slice, but this slice may also be changed. In this case or even if, as explained above, the light-guiding facility is not anyway permanently adjusted to the (fixed) slice orientation, the actuating unit of the processing facility may be configured to actuate the light-guiding facility for projecting the orientation line according to the current representation orientation.

The light pattern includes a further projection line that is for example perpendicular to the orientation line. Such a further projection line may, for example, indicate the center of the imaging facility, for example in the case of a computed tomography facility. However, it may also be suitably adjustable via a corresponding actuator, for example to indicate a current longitudinal direction of at least the proximal portion of the medical instrument. It is furthermore conceivable to adapt the relative position and orientation of the further projection line by actuating the adjustable patient bench.

In an embodiment, the light pattern for marking the projection point on the orientation line includes an orientation point that may for example be adjusted in an actuatable manner by the processing facility on the basis of the positioning information. Such an orientation point that indicates a position along the orientation line may, for example, be specified in a simple manner by a laser beam of a corresponding laser light source of the light-guiding facility. Here, it is particularly expedient if the orientation line and the orientation point have different colors. For example, a green orientation point may be used with a red orientation line. Herein, the orientation point could be understood as an extended shape that is particular at least substantially circular, wherein a small projection element is preferred here for simple implementation. For example, the orientation point may also be a short orientation bar that may migrate along the orientation line. The position of the orientation point along the orientation line may be adjusted by actuation by the actuating unit of the processing facility. The provision of such an orientation point is easy-to-implement, especially if the lateral fixability of the patient bench is not sufficient in the case of a self-adjustable further projection line indicating the center of the imaging facility.

In an embodiment, the markings have at least one alignment line to be brought into coincidence with the orientation line, for example in such a way that, if the projection point remains on the alignment line brought into coincidence, the medical instrument remains in the image plane or slice represented in the representation. This is for example expedient when an axial slice of a reconstructed computed tomography image is to be used as image data, as already explained above. In order to be able to bring the alignment line and the orientation line into coincidence, the alignment element may be arranged rotatably on the medical instrument; however, it is also conceivable that the medical instrument rotates about its longitudinal axis.

The alignment line together with the orientation line provide the user with intuitive orientation that makes it easier not only to interpret the representation, but also to assign markings to correctly represented continuation trajectories. This may also be expedient if, as is usually the case, if work is not performed in the represented slice, but it is intended to move out of it. Usually, however, work is performed in a specific slice in order also to simplify the further imaging, for example on renewed capturing of image data.

Here, the alignment element may also be configured for this work in a specific slice. For example, it may be provided that markings that may be assigned to continuation trajectories are provided along the alignment line, so that when the alignment line is brought into coincidence with the orientation line, for each position correction, the medical instrument remains in a slice marked by the orientation line. Here, the alignment element may expediently be configured as elongate in the direction of the alignment line. This embodiment has proven to be particularly useful in conjunction with the use of a projection point, since then the extension of the light pattern is also mainly in the direction of the orientation line. In order to undertake a position correction within the slice, that also corresponds to the image plane of the representation, it is then only necessary to bring the alignment line into coincidence with the orientation line of the light pattern and to bring the projection point to the corresponding marking along the alignment line that corresponds to the selected continuation trajectory according to the marking information in the representation.

Embodiments in the context of the first embodiment may furthermore provide that the markings form at least part of a crosshair including the at least one alignment line, the center of which coincides with the projection point before the position correction is undertaken, and the rings of which, for example in different colors, are assigned to respective continuation trajectories, and/or the markings form a coordinate grid, for example a matrix-like grid, wherein coordinates are assigned at least to markings that may be assigned to the continuation trajectories.

A crosshair has the advantage that the orientation line may be quickly and easily brought into coincidence with one of the (then two mutually perpendicular) alignment lines, for example if work is to be performed permanently in a specific slice anyway. For example, the markings may then form colored circles of the crosshair, wherein the projection point may then be moved in a desired direction on the selected alignment line brought into coincidence with the orientation line to a desired marking of a desired color specified by the marking information for position correction. When working within a slice that also forms the image plane of the representation, expediently, in each case two continuation trajectories of a color, for example the color of a circle of the crosshair, may be determined anyway, namely one for each correction direction within the slice. The intuitive orientation by the orientation line makes it easy for the user to correctly assign the corresponding directions of the correction within the slice.

When using markings in a matrix-like coordinate grid, for example marking points or marking circles, in a regular matrix arrangement, it is, for example, possible for coordinate information to be used as marking information, for example in such a way that, for a B3 continuation trajectory, the projection point is to be moved accordingly to the marking in the coordinate grid at B3. However, even if the projection point cannot be arranged in the center, i.e., does not necessarily always indicate the same direction, for example the longitudinal direction of at least the proximal portion of the medical instrument, a coordinate grid is extremely useful, because then, for example, a relative assignment may be made in the coordinate grid, for example of the type "one to the right, three down".

In the second embodiment, a different approach is selected in which the light pattern, for example the projection point, indicates the place to which the (possibly then one) marking is to be moved. This means that, in this embodiment, it is provided that the alignment element has only one marking defining an alignment point and the processing facility is configured to actuate the light-guiding facility for marking a projection point assigned to the continuation trajectory on the projection surface, that is to be brought into congruence, i.e., coincidence, with the alignment point in order to select the assigned continuation trajectory. Such an embodiment is for example expedient if a continuation trajectory leading to a target area or instrument target in the intervention area is ascertained and this trajectory is to be adhered to as precisely as possible. The projection point may then indicate the place to which the alignment point defined by the at least one marking is to be moved in order to perform the position correction for achieving this selected continuation trajectory. A plurality of distinguishable projection points assigned to different continuation trajectories may be projected as part of the light pattern. In other words, projection points may have distinguishable optical properties that are described by the marking information or their marking information may correspond in its distinguishable optical properties to the distinguishable optical properties of the projection points, so that a continuation trajectory may be selected according to the representation by moving the alignment point to the corresponding projection point.

In the second embodiment, the actuating unit is required as part of the processing facility in order to actuate the light-guiding facility and/or a patient bench such that the at least one projection point correctly indicates the respective continuation trajectory.

Actuators assigned to laser light sources, for example for adjusting laser beams projected into the room or crossed laser planes, are actuated such that the displacement of the proximal end of the medical instrument is indicated by the projection point, that has to be realized as a position correction in order to realize a specific continuation trajectory selected, for example, by user input and/or automatically. In other words, the light pattern is displaced and indicates the desired degree of bending of the medical instrument as a new projection point.

Thus, in the second embodiment, a simply configured alignment element is sufficient and continuation trajectories, for example continuation trajectories leading best to an instrument target, may be adjusted with high precision, intuitively and easily.

A targeted selection of one of a plurality of continuation trajectories implemented by user input is conceivable for both embodiments. For example, in the second embodiment, the user may select a continuation trajectory from a plurality of proposals, for which the projection point then indicates the necessary position correction. For example, in the first embodiment, it may be provided that the marking information is only inserted in the representation once this selection has been made, for example with regard to a coordinate grid for which an output for a relative displacement in the coordinate grid may then take place.

Embodiments provide where the proximal portion has a point of application for manually undertaking the position correction. The evaluation unit is configured to take account of the location of the point of application when ascertaining the at least one continuation trajectory. Herein, the point of application provided is preferably located at the proximal end of the instrument and/or adjacent to the alignment element and/or on the alignment element, wherein, however, other application points are also conceivable. Depending on the location of the point of application, i.e., where the user grips the medical instrument for position correction, other shapes occur at the proximal portion, for example with regard to bending, that, may be optimally taken into account with knowledge of the point of application and included in the ascertaining of the continuation trajectories. The further out the point of application is located, the more the benefit from the bending properties of the instrument. In embodiments in which different application points are provided or may be used, the point of application currently being used may, for example, be derived from user input.

In an embodiment, the intervention device may include an imaging facility for capturing at least part of the image data. Such intervention workstations, that also already have an imaging facility, for example for monitoring the intervention, have in principle already been proposed in the prior art. Here, the processing facility may also include a capturing unit to actuate the imaging facility to capture the image data. A computed tomography facility may be used since this is already in principle known for example for guided interventions with elongate medical instruments, for example needles, and procedures may be adopted, for example when performing planning. A computed tomography device provides three-dimensional image data, for example for an axial slice including the intervention area, in a simple and quick manner, that for example also clearly depicts the instrument and is thus easy to evaluate. In addition to a computed tomography facility, alternatively or additionally, other imaging facilities, for example X-ray facilities, may be used. The imaging facility may, for example, also be a C-arm X-ray facility with a C-arm on which an X-ray emitter and an X-ray detector are arranged opposite one another. The degrees of freedom of movement of the C-arm enable adjustment to different projection geometries/capturing geometries. In principle, further imaging modalities may be used.

With regard to a C-arm X-ray facility or an X-ray facility allowing different capturing geometries, it may be noted that fluoroscopic monitoring usually takes place here. Herein, the capturing geometry, for example the angulation of the C-arm, may be changed in order to be able to recognize the instrument path in all spatial directions. Typical examples of interventions performed under fluoroscopic observation are bone biopsy, spinal fusion and vertebroplasty. In order to ascertain the image data from which conclusions are to be drawn about the positioning of the instrument and/or the anatomy, in such cases, it may be provided that fluoroscopic images of the medical instrument are captured from at least two projection directions in order to obtain the desired three-dimensional information. However, it is also conceivable to undertake C-arm CT acquisition.

The light-guiding facility may be permanently installed on the imaging facility and/or integrated therein. This is already known for computed tomography facilities when performing minimally invasive interventions with elongate instruments, for example needles, in order to implement an instrument guidance system and/or offer a user optimal orientation, for example by indicating the orientation of the axial slice (for example by the orientation line) and/or the center of the imaging facility. Here, the light-guiding facility may, for example, be arranged on the gantry. This is also in principle possible with a C-arm, for example, by returning to the so-called "bull's eye view" after capturing of the image data at different angulations in which the light-guiding facility or the light pattern is aligned with the orientation point along the longitudinal axis of at least the proximal portion of the instrument. For example, in this case, the light-guiding facility, for example the laser guidance facility, may be arranged on the X-ray detector, as described, for example, in the publication "Improved Laser Needle Guidance" by Dr. Alois Regensburger et al., Siemens AG 2019.

As already mentioned, the evaluation unit may be configured to ascertain the positioning data at least partially from the image data. This means no additional positioning data is required and/or this may be checked for plausibility. For example in the case of X-ray imaging, such detection of the instrument and the ascertaining of the positioning data is easily possible using common algorithms, since the medical instrument represents a high-contrast object.

The evaluation unit may be configured to register the image data with provided preliminary image data of the examination object. For example, in the case of fluoroscopic images, the anatomy, that is also of interest, is sometimes less clearly mapped in X-ray imaging, whereas it may be easily recognized or segmented in preliminary image data. Therefore registration to such a preliminary image dataset, for example a three-dimensional computed tomography image dataset/or magnetic resonance image dataset, is possible, wherein, in the preliminary image dataset, the anatomy, for example different types of tissue, may already be segmented or mechanical properties may be assigned to segmented areas. Anatomical information describing the current state of the anatomy in the intervention area is ascertained directly from the image data in order, for example, to follow any displacements and/or other movements that have occurred. Such anatomical information may also be used to update the preliminary image dataset, for example with regard to tissue boundaries. This may also be done by the registration itself if elastic registration is performed with regard to the anatomy in the intervention area. If the image data also depicts the anatomy sufficiently clearly, an elastic registration ultimately leads directly to information about changes that have occurred.

The image data showing the current situation with a partially inserted medical instrument may be that of a control scan. In the context of the evaluation, as already explained, the positioning data may be ascertained from the image data. The following evaluation information may be obtained by evaluating the image data (for example together with rigid or preferably elastically registered preliminary image data) for example using standard image evaluation methods, for example including segmentation and/or position determination and/or detection of structures: positioning information (location of the instrument, shape of the instrument (for example centerline along the instrument and/or functional approximation of the shape of the instrument) and locations of the distal and, if visible, proximal end of the instrument), entry point of the instrument into the examination object and portions of the instrument that are located within and outside the examination object (if the proximal portion of the instrument located outside the examination object is not or not completely contained in the image data, the course may be extrapolated to the proximal end assuming a force-free, i.e., not actively deflected, location of the instrument, for which purpose the property data may expediently also contain further information on the medical instrument, for example on the length and the like), and/or anatomical information, for example including the current location of anatomical structures, for example organs and their organ boundaries, for example including the target area. Furthermore, elasticity and/or mobility of the anatomical structures may be known or assumed.

The location of an originally planned instrument trajectory (planning trajectory) may also be tracked in the image data, for example when registered with preliminary image data on which the planning was based.

Based on the information available, a simulation and/or model calculation may then be carried out to determine how a position correction, including bending of the instrument, at the rear (proximal) end of the instrument would affect the location and shape of the instrument within the patient and the trajectory at the front (distal) end of the instrument (with further advancement). Herein, the property data describing the bendability of the medical instrument (for example in both the proximal portion and distally) are also taken into account. Here, the property data for example includes mechanical and/or elastic parameters of the instrument. As mentioned, the mechanical properties may also be known or assumed for the anatomy.

The evaluation unit may be configured to ascertain the property data from provided instrument information. Herein, the instrument information may, for example, describe a model and/or a kind and/or a type of the instrument. For example, the property data may be assigned to the instrument information in a database and/or a look-up table (LUT). Standard assumptions may be made for the property data.

In addition to the at least one continuation trajectory, the evaluation unit may also be configured to ascertain a future trajectory resulting without position correction and the output unit may be configured to indicate the future trajectory in the representation. In this way, the user also receives information about the development of the instrument path if no position correction is undertaken. The continuation trajectories may for example be intuitively and easily compared with the future trajectory and evaluated with regard to reaching the target area.

The evaluation unit may be configured to ascertain a recommendation for an advancement distance and the output unit to be configured to output this. For example, the reliability of the advance calculation of the continuation trajectories may be ascertained. Advancement may be recommended up to a specific threshold value of the reliability of the advance calculation. After advancement by the recommended advancement distance, that may be given in centimeters, for example, expediently, new capturing of image data, i.e., a new control scan, may take place and new continuation trajectories for position corrections may be ascertained.

In addition to the intervention device, embodiments further relate to a computer-implemented method for ascertaining and outputting a positioning instruction for an elongate medical instrument, that may be partially inserted into an intervention area of an examination object for an intervention, has a proximal portion to be arranged outside the examination object for manual handling of the medical instrument and is at least partially bendable, wherein an alignment element arranged on the instrument and/or integrated therein, that has a projection surface with at least one marking that marks at least one point, is used, wherein, when the instrument is already partially inserted into the examination object, the method has the following steps: providing image data of the examination object representing the intervention area via an interface of a processing facility and ascertaining positioning data describing the current position and location of the medical instrument, using an evaluation unit of the processing facility to ascertain at least one predictive, for example non-linear, continuation trajectory from the image data and the positioning data using property data describing the bendability of the medical instrument, outputting a representation of the intervention area based on the image data and the at least one continuation trajectory by an output unit of the processing facility on a representation facility; and for example by an actuating unit of the processing facility, operating a light-guiding facility for projecting at least one light pattern onto the projection surface in such a way that a combined view of at least one of the at least one marking and the light pattern produces the positioning instruction for manual position correction at the proximal portion of the medical instrument in order to achieve one to be selected of the at least one continuation trajectory upon further insertion of the medical instrument.

All explanations relating to the intervention device may be transferred analogously to the method, that may also be referred to as an instruction method, and vice versa, so that the advantages already mentioned may be obtained. For example, the positioning data is ascertained by the evaluation unit using the image data. The method may also include the step of capturing the image data, controlled by a capturing unit.

The positioning instruction may be understood as a workflow instruction, so that a support or decision-making aid is created for the user, that is provided after positioning of the medical instrument, for example in the context of a control scan that provides the image data. Therefore, reference is made to the fact that, even when used in the context of an intervention on a patient, no guidance, advancement or other action is performed on the medical instrument in the examination object in the context of the instruction method.

As already explained above for the intervention device, embodiments are also provided for the method. The light pattern may mark a projection point that, to select the selected continuation trajectory, is to be brought into congruence with a marking assigned to the selected continuation trajectory, wherein the representation is generated with marking information assigned to the at least one continuation trajectory and describing the assigned marking. Alternatively or additionally, the alignment element has only one marking defining an alignment point and the processing facility actuates the light-guiding facility for marking a projection point on the projection surface assigned to a continuation trajectory, wherein, for selecting the assigned continuation trajectory, the projection point is to be brought into congruence with the alignment point.

The instruction method may be integrated into a method for treating and/or examining an examination object by a elongate medical instrument, that is partially inserted into an intervention area of an examination object for an intervention, has a proximal portion to be arranged outside the examination object for manual handling of the medical instrument and is at least partially bendable, wherein for ascertaining and outputting a positioning instruction after the insertion of the instrument into the examination object an alignment element arranged on the instrument and/or integrated therein, that has a projection surface with at least one marking that marks at least one point, is used, image data of the examination object representing the intervention area is provided via an interface of a processing facility and positioning data describing the current position and location of the medical instrument are ascertained, by an evaluation unit of the processing facility, at least one predictive, for example non-linear, continuation trajectory is ascertained from the image data and the positioning data using property data describing the bendability of the medical instrument, a representation of the intervention area and the at least one continuation trajectory based on the image data is output by an output unit of the processing facility on a representation facility; and for example by an actuating unit of the processing facility, a light-guiding facility for projecting at least one light pattern onto the projection surface is operated in such a way that combined viewing of at least one of the at least one marking and the light pattern produces the positioning instruction for manual position correction at the proximal portion of the medical instrument for achieving at least one to be selected of the at least one continuation trajectory upon further insertion of the medical instrument, after which the positioning instruction is manually implemented by a person performing the intervention at the proximal portion of the instrument, for example at the point of application, and the instrument is pushed further into the examination object.

The method may be performed iteratively, that means that, after a certain, for example recommended, advancement distance of the instrument, new image data may be captured/provided and used as the basis for generating and outputting a further positioning instruction with the instruction method.

A computer program may be loaded directly into a memory a processing facility of an intervention device and has programming code, that, when the computer program is executed, cause the processing facility to perform the steps of an instruction method. The computer program may be stored on an electronically readable data carrier, which therefore includes control information thereon, that includes at least one computer program and is configured in such a way that, when the data carrier is used in a processing facility of an intervention device, it is configured to execute an instruction method.

DETAILED DESCRIPTION

Figure 1:
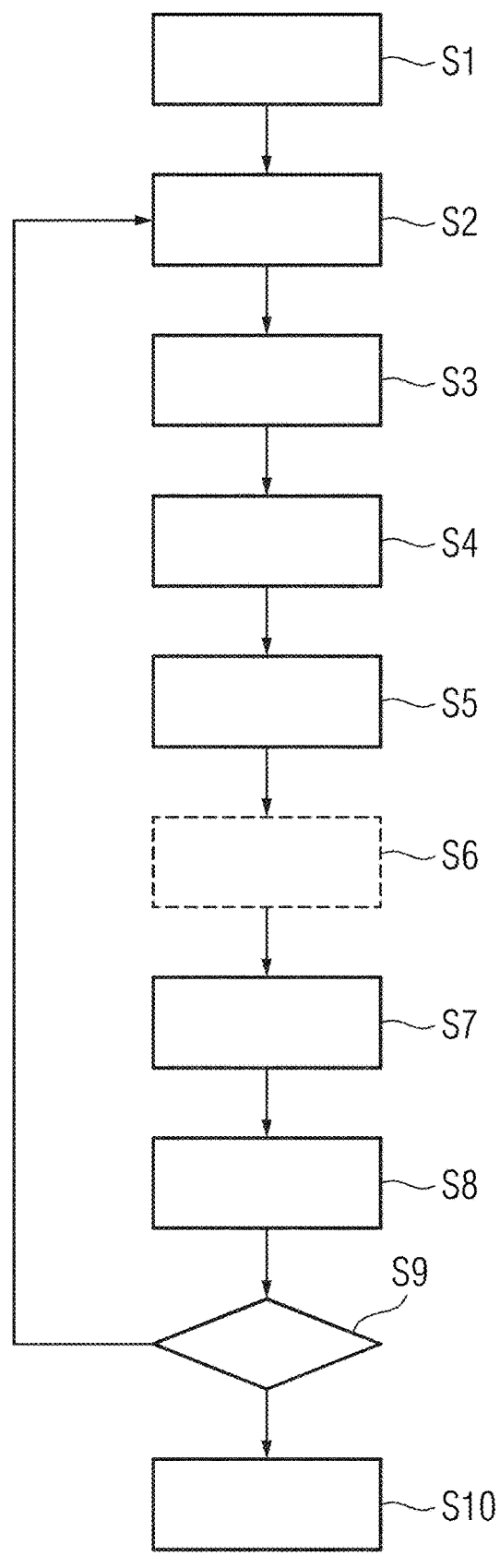
FIG. 1 depicts a flow chart of an embodiment of the method according to an embodiment.

FIG. 1 depicts a flow chart of an embodiment of the guidance of a medical instrument, here a needle, to a target area, that includes an instruction method in steps S2 to S7.

In a step S1 performed before the start of the instruction method, the medical instrument is inserted into the examination object, for example a patient or an examination phantom. This may take place according to a pre-planned instrument trajectory, i.e., a planning trajectory, that, as is known in principle, was planned on planning image data (that may correspond to the preliminary image data mentioned later). Here, the planning trajectory may be adjusted by laser guidance by a light-guiding facility, that is also used in the following instruction method, and the medical instrument is inserted a little way into the examination object according to this planning trajectory. However, this process, but also other (intentional or unintentional) movement processes in the intervention area, that also contains an instrument target (target area), may also lead to changes so that the target area is not necessarily reached with the planning trajectory.

However, planning is not necessarily required with the procedure presented here, that means that a user, for example a physician, may initially advance the medical instrument by a first distance without guidance or under live imaging and still reliably reach the target area based on the instruction method that now follows.

In a first step of the instruction method, step S2, when the medical instrument has already been partially inserted into the examination object, image data of the intervention area is captured with the instrument as a control scan by an imaging facility controlled by a capturing unit of a processing facility of the intervention device with which the intervention is performed. Here, this may be three-dimensional capturing, for example a computed tomography scan, however, it is also conceivable to capture one or more two-dimensional images as image data, for example, when using a C-arm-X-ray facility, two-dimensional X-ray images (for example fluoroscopic images) from different projection directions (angulations), i.e., with different capturing geometries. If necessary, the capturing may also include the reconstruction of images, for example an axial slice image that maps the intervention area in computed tomography.

If preliminary image data, for example three-dimensional image data, of the intervention area is available, the image information of which is useful for the following evaluation, a rigid or elastic registration of image data to the preliminary image data may also take place, for example the planning image dataset. In the case of elastic registration, the registration transformations already contain information on any deformations of the anatomy that may have occurred in the intervention area; with rigid registration, only simple translatory movements may be inferred.

In step S3, the image data is then evaluated using standard evaluation methods, for example together with the preliminary image data registered for this purpose, in an evaluation unit of the processing facility. For example, segmentation algorithms, position-determining algorithms, classification algorithms, detection algorithms and the like may be used.

In the context of the evaluation, initially positioning information regarding the elongate, at least partially elastically bendable, medical instrument is ascertained. This may, for example, include the location of the medical instrument, the shape of the medical instrument (which here has a certain bendability) (for example as a centerline and/or as functional description of the shape), positions of the distal and the proximal end of the instrument, wherein, if the proximal portion of the instrument located outside the examination object is not visible or only partially visible in the image data, the proximal end may nevertheless be estimated on the basis of known properties of the instrument (for example its length) assuming freedom from forces, and/or the puncture point (entry point) of the medical instrument in the body of the examination object and portions of the medical instrument located within (distal portion) and outside (proximal portion) the examination object.

In step S3, anatomical information may furthermore be determined by evaluating the image data, for example the location of the target area (instrument target), the location of anatomical structures and/or boundaries of organic structures (for example organs) and/or the location of the planning trajectory in the anatomy, if present.

The anatomical information may be determined at least partially taking into account the registered preliminary image data, for example if these anatomical structures are already segmented and/or marked in the preliminary image data.

In step S4, a simulation and/or model calculation is then performed to determine how a position correction at the proximal portion of the instrument, for example at the proximal end of the instrument, including a bending of the instrument, affects the location and shape of the instrument within the examination object, i.e., the distal portion. For example, here, it is calculated in advance what would result as a continuation trajectory if position correction and advancement of the medical instrument were present. In addition to these position corrections and the assigned continuation trajectories, a future trajectory of the medical instrument resulting without position correction is also calculated in advance, that results if the medical instrument is advanced without position correction at the proximal end. All these calculations take into account the bendability of the medical instrument, i.e., property data describing this elastic bendability of the medical instrument. Such property data may, for example, include mechanical parameters and/or elasticity parameters. While the property data may be based on a standard assumption, it is preferable for this to be retrieved, for example from a database and/or a look-up table in dependence on provided instrument information, for example inferred from user input. The instrument information may, for example, describe a model and/or a kind and/or type of the medical instrument.

The position corrections for which the at least one continuation trajectory is ascertained and the way in which it is ascertained depend on the specific approach selected. If an alignment element with a projection surface is provided on the medical instrument on which a plurality of different markings describing known position corrections in the evaluation unit are provided, continuation trajectories may be ascertained for all these markings and the assigned position corrections. However, if a specific position correction is proposed on the projection surface, for example by a light pattern of the light-guiding facility that may be actuated by an actuating unit, this may also be ascertained, for example in an optimization method, in such a way that the target area is reached as precisely as possible.

Finally, for each of the continuation trajectories individually or for all continuation trajectories as a whole, in step S4, a recommended advancement distance until the next control scan may be ascertained, for example in dependence on a reliability value indicating the reliability of the advance calculation over this distance for the continuation trajectory or continuation trajectories.

In all of these evaluations, the location of the point of application for undertaking the position correction at the proximal portion of the instrument is also taken into account. Here, a location of the point of application at the proximal end of the medical instrument is preferable. Depending on the location of the point of application, other shapes, for example bends, of the proximal portion may occur and these are taken into account accordingly.

In step S5, a representation is generated by an output unit of the processing facility and output by a representation facility, for example a monitor that may be easily viewed by a person manually operating the medical instrument. The representation is based on the image data, for example the aforementioned axial slice image, and therefore has a specific representation orientation (as the image plane of the image data in the representation). The image data also allows the representation to show the medical instrument and the anatomy in the intervention area, wherein both the medical instrument and anatomical structures, for example if they are segmented and their boundaries are known, may be highlighted and/or contrasted for better recognizability. Corresponding methods for generating suitable representations are known. In each case, the representation also contains graphical elements, for example by overlaying, that insert the at least one continuation trajectory and the future trajectory at a precise location. If a recommended advancement distance is ascertained, this may also be output. This will be discussed in more detail below with regard to the different embodiments.

In step S6, at least one of the continuation trajectories may be selected on the basis of user input. This is for example expedient if a plurality of continuation trajectories have been ascertained and a selection option by identifying a suitable marking or a suitable distinguishable projection point, that will likewise be discussed below, is not provided. The selection may for example be made by assessing the continuation trajectories in the representation.

In step S7, a positioning instruction for adjusting a corresponding manual position correction at the proximal portion of the medical instrument for reaching one to be selected of the at least one continuation trajectory is output upon further insertion of the medical instrument. The positioning instruction is produced by a combined view of a light pattern emitted by the light-guiding facility on the projection surface, the at least one marking on the projection surface and possibly the representation. Since different approaches may be used for this in the instruction method, these will be explained in more detail with regard to FIGS. 4 to 23.

In a step following this instruction method, the person performing the intervention, i.e., the user, may undertake the position correction following the positioning instruction, i.e., create the conditions for the selected continuation trajectory and then further advance the medical instrument in the direction of the instrument target, for example by the recommended advancement distance.

In step S9, a check may then be performed to see whether the instrument target, i.e., for example the target area, has been reached and whether it is possible to continue with the reason for the intervention, so that the actual reason for the intervention may be executed in step S10. Otherwise, the instruction method, steps S2 to S7, is executed again including a new control scan, in order to support the user in reaching the instrument target. It may be noted that the control scan may obviously be performed as the basis of step S9.

Figure 2:
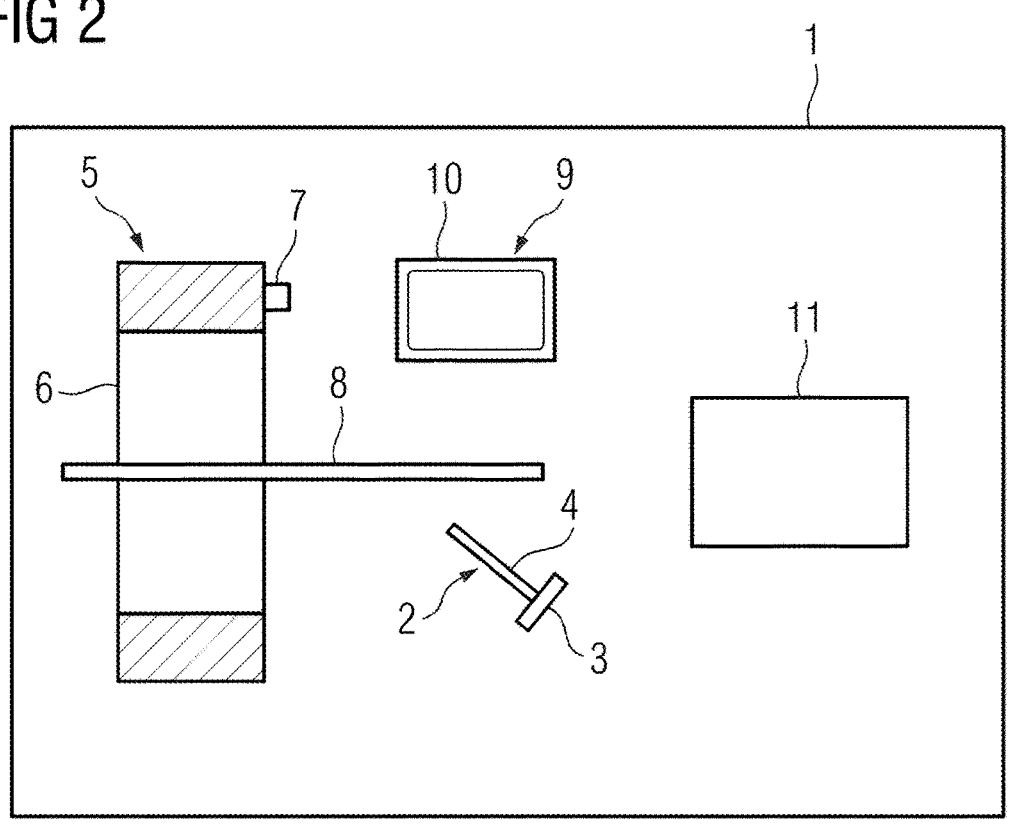
FIG. 2 depicts a schematic sketch of components of an intervention device according to an embodiment.

FIG. 2 is a schematic sketch showing components of an intervention device 1. The intervention device 1 initially includes the medical instrument 2 to which the alignment element 3 is attached or into which the alignment element 3 is integrated. The medical instrument 2 is configured as a needle 4. In the present case, the imaging facility 5 is a computed tomography facility with a gantry 6 on which, in the present case, the light-guiding facility 7 is arranged. The light-guiding facility 7 may have one or more laser light sources for generating laser fans and/or laser beams, so that the light pattern is created with corresponding alignment on the projection surface. The examination object may be moved into the gantry 6 by a patient bench 8.

In the present case, the representation facility 9 is configured as a monitor 10.

Figure 3:
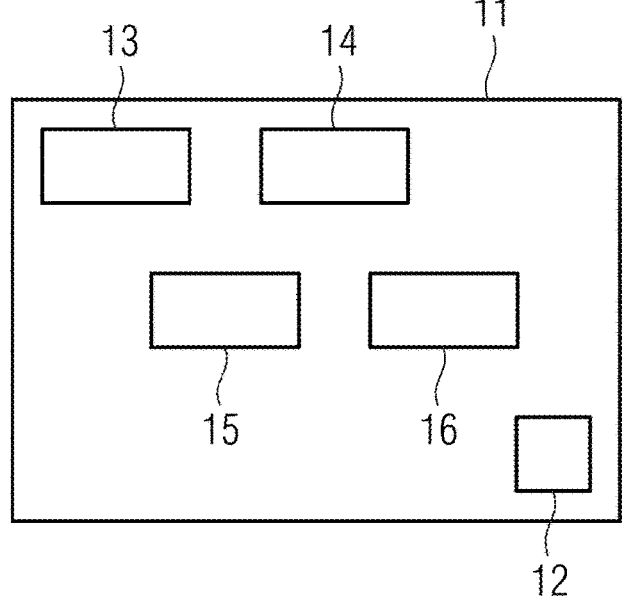
FIG. 3 depicts the functional structure of the processing facility of the intervention device according to an embodiment.

The operation of the intervention device 1, for example for performing the instruction method, is controlled by the processing facility 11, the functional structure of which is shown in more detail in FIG. 3. In addition to a memory 12, the processing facility 11 initially includes a capturing unit 13 for actuating the imaging facility 5 for capturing the image data and possibly for registering it with preliminary image data and/or for the reconstruction of volumes and/or slice images, in the present case for example axial computed tomography-slice images. In other words, the capturing unit 13 is configured to perform step S2. The evaluation unit 14 is configured to evaluate the image data and to ascertain the continuation trajectories and possibly the future trajectory and the recommended advancement distance according to steps S3 and S4. The output unit 15 serves to generate and output the representation according to step S5, while the actuating unit 16 is configured to actuate the light-guiding facility 7, for example in the context of step S7. Other further functional units or sub-functional units may be used.

Figure 4:
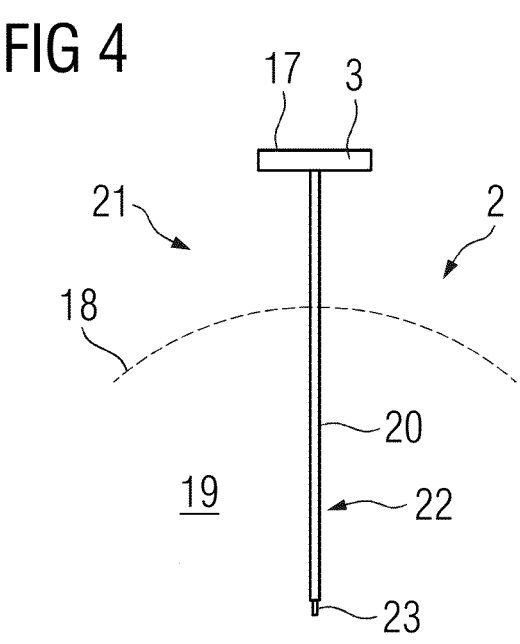
FIG. 4 depicts a detailed schematic view of a medical instrument for a first embodiment.

FIG. 4 is a schematic view of the instrument 2 to which the alignment element 3 is attached, in the present case at the proximal end. On its upper side, the alignment element 3 forms the projection surface 17. If the dashed line 18 is assumed to be the boundary of the examination object 19, the medical instrument 2, that, in the present case, has an elongate elastically bendable instrument shaft 20 as a needle 4, has a proximal portion 21 and a distal portion 22 with the distal end 23, that is intended to reach the instrument target, i.e., the target area.

Figure 5:
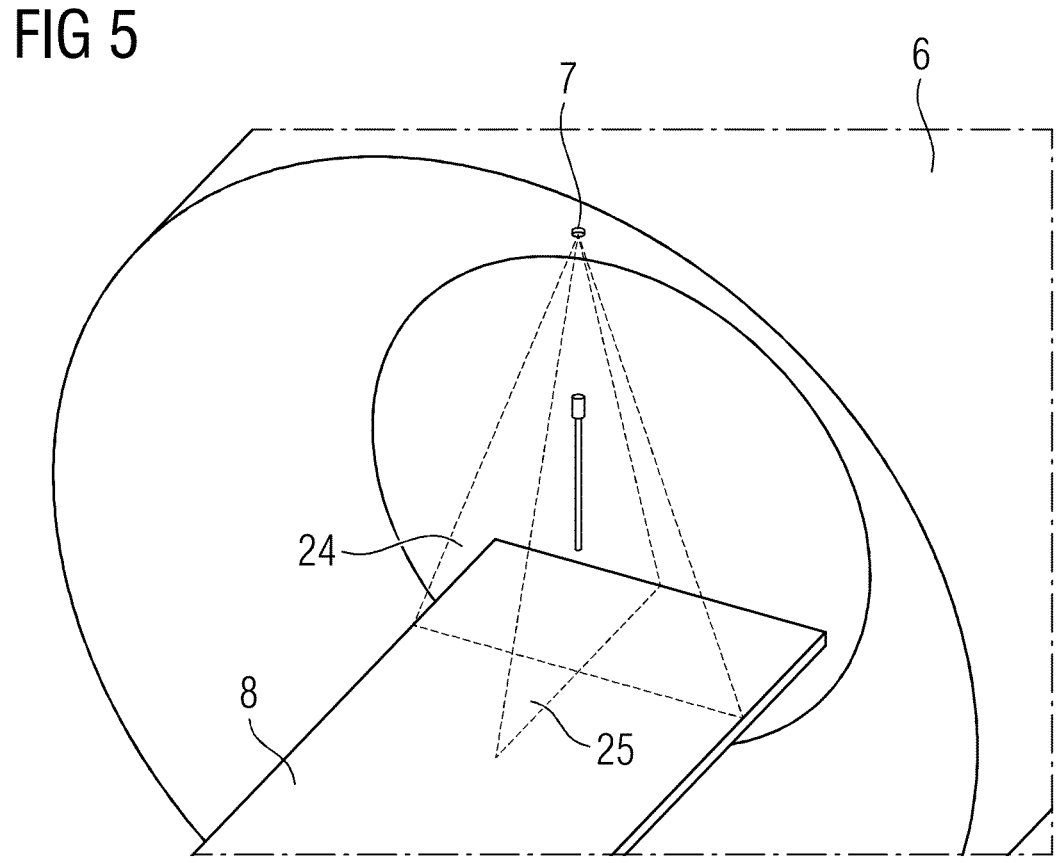
FIG. 5 depicts a light-guiding facility for the first embodiment of FIG. 4.

FIG. 5 depicts by way of example a possible embodiment of the light-guiding facility 7 on the gantry 6. In the present case, the light-guiding facility 7 has laser light sources for generating two laser fans 24, 25, wherein for example, at least in the basic mode of the imaging facility 5, the laser fan 24 may indicate the location or orientation of the reconstructed axial slice on the examination object in the form of an orientation line. The laser fan 25 may indicate the center of the gantry 6 or the imaging facility 5. Actuators may be assigned to the laser light sources in order to adjust the laser fans 24 and 25; the relative position may also be adapted by actuating the patient bench 8 by the actuating unit 16.

Other embodiments of the light-guiding facility 7 may be used in order to be able to project suitable light patterns onto the projection surface 17 for the embodiments discussed in more detail below. For example, a laser light source may also be provided for projecting a laser beam and thus an orientation point in addition to the orientation line.

A first embodiment for which some embodiments will now be explained provides that the light pattern marks a projection point that is to be brought into congruence with a marking assigned to the selected continuation trajectory for the selection of the selected continuation trajectory. For this purpose, the output unit 15 is configured to generate the representation with the marking information assigned to the at least one continuation trajectory and describing the assigned marking. Herein, in the embodiments of the first embodiment represented in the following, it is expedient to work within the slice of the axial slice image, that also forms the basis of the representation.

Figure 6:
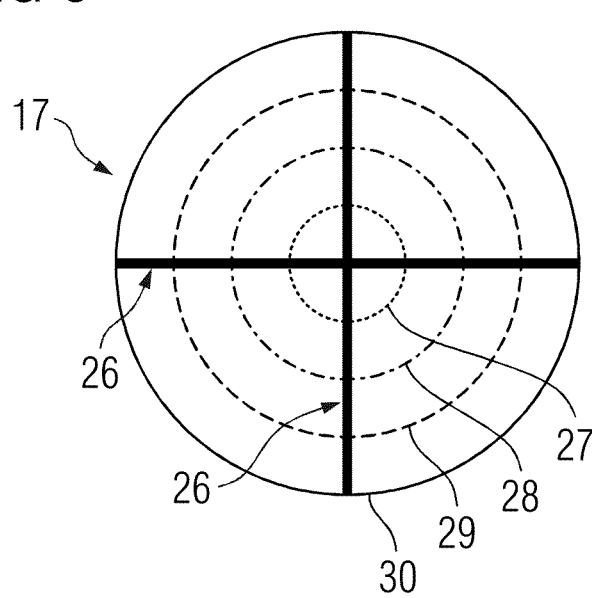
FIG. 6 depicts an alignment element for the first embodiment of FIG. 4.

FIG. 6 depicts a possible embodiment of the projection surface 17 of the alignment element 3 for a first embodiment. This has markings in the manner of a crosshair, wherein the cross is formed by two alignment lines 26 extending perpendicular to one another. Concentric circles or rings 27, 28 and 29 extend around the center point of the cross that are applied in different colors (as a different optical property), for example the circle 27 in green, the circle 28 in blue and the circle 29 in violet. The circle 30 represents the outer edge. It may be seen that the circles 27 to 29 cross the alignment lines 26 several times.

Figure 11:
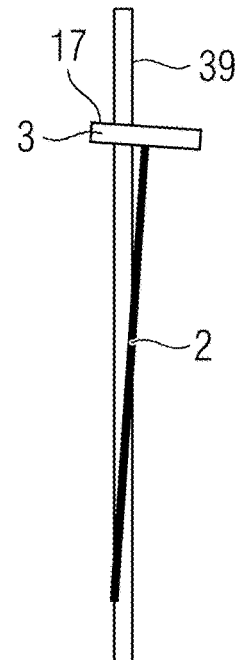
FIG. 11 depicts an illustration of the instruction in a third state of the instrument and alignment element according to an embodiment.
Figure 12:
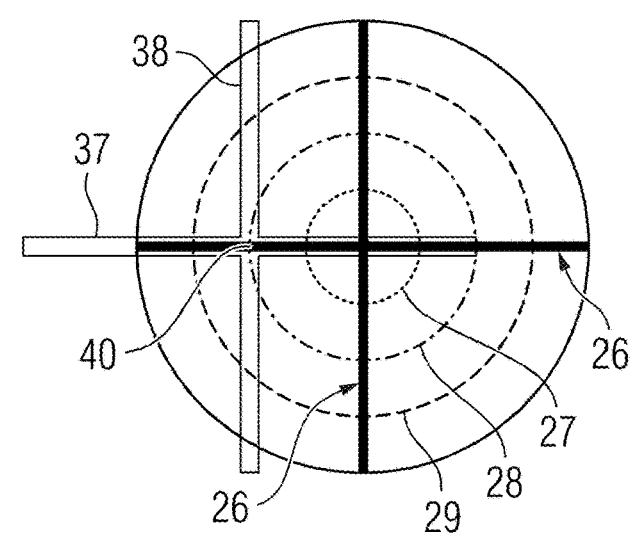
FIG. 12 depicts an illustration of the third state on the projection surface according to an embodiment.
Figure 13:
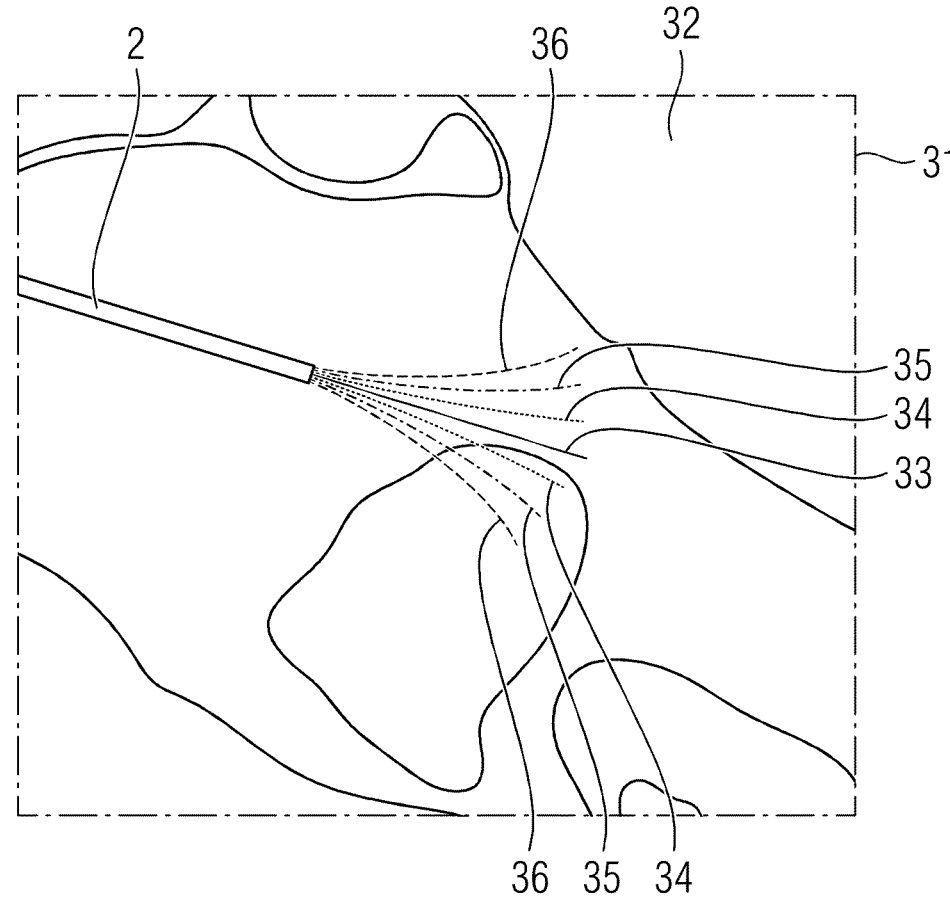
FIG. 13 depicts a representation associated with the first embodiment for output on a representation facility.

FIGS. 7 to 12 describe the use of this alignment element 3 for outputting the positioning instruction, wherein FIG. 13 reproduces a possible representation 31 on the representation facility 9. The representation 31 is based on image data 32 in which the anatomy and the medical instrument 2 are partially visible. The central graphical element 33 depicts the future trajectory, the graphical elements 34, 35, 36 adjacent thereto in both directions indicate continuation trajectories. Here, the graphical element 33 is in a color, for example orange, that does not occur in the circles 27, 28 and 29, while the distinguishable optical property of the graphical elements 34, 35 and 36 in each case corresponds to that of the circles 27, 28 and 29. In other words, the graphical elements 34 are green, the graphical elements 35 are blue and the graphical elements 36 are violet. Therefore, the graphical elements 34, 35 and 36 not only indicate the course of the continuation trajectories, but also contain marking information (the color) in order to be assigned to corresponding markings on the projection surface 17 of the alignment element 3.

This provides—with the direction in which the corresponding continuation trajectory deviates from the future trajectory—a clear assignment to markings if it is intended to remain in the slice of the axial slice image.

Figure 7:
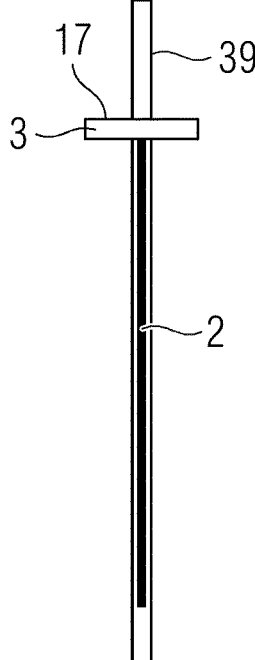
FIG. 7 depicts an illustration of the instruction in a first state of the instrument and alignment element according to an embodiment.
Figure 8:
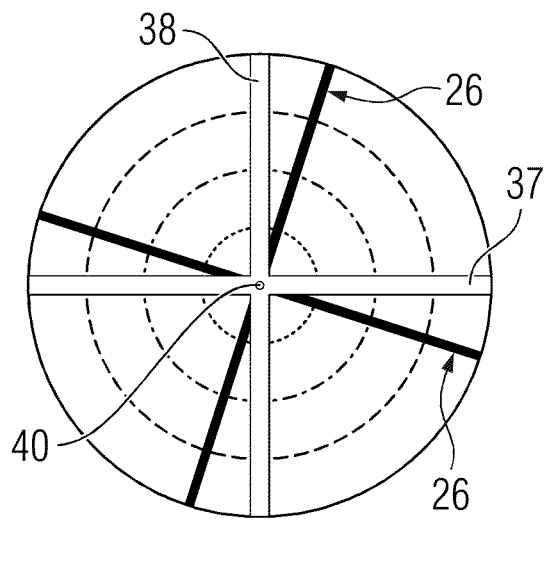
FIG. 8 depicts an illustration of the first state on the projection surface according to an embodiment.

FIG. 7 and FIG. 8 now represent a first situation in which the light pattern, that, in the present case, see FIG. 8, is formed by an orientation line 37 and a projection line 38 perpendicular thereto, likewise forms a cross, that however does not coincide with the cross of the alignment lines 26 of the crosshair. The orientation line 37 indicates the representation orientation, i.e., the orientation of the image plane of the axial slice image, and may be easily identified by the user in the context of the imaging facility 5 and the arrangement of the examination object 19 on the patient bench 8. Actuation of the light-guiding facility 7 and/or the patient bench 8 causes the direction of the crossing beam 39, see FIG. 7, to coincide with the longitudinal direction at least of the proximal portion 21 of the instrument 2, so that the crossover point of the light pattern from the orientation line 37 and the projection line 38, that represents a projection point 40, and the crossover point of the alignment lines 26 correspond.

Figure 9:
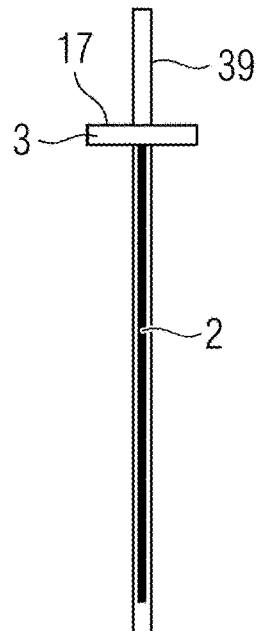
FIG. 9 depicts an illustration of the instruction in a second state of the instrument and alignment element according to an embodiment.
Figure 10:
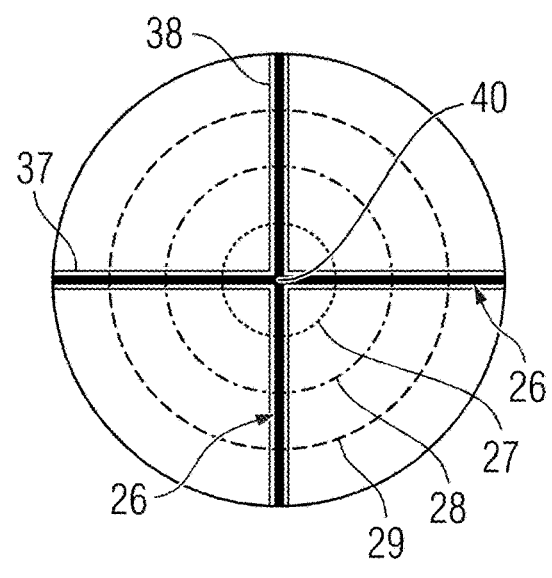
FIG. 10 depicts an illustration of the second state on the projection surface according to an embodiment.

As represented in FIGS. 9 and 10, the user rotates the alignment element 2 in such a way that, see FIG. 10, one of the alignment lines 26 comes to lie on the orientation line 27, wherein the other alignment line 26 then lies on the projection line 38. The intersection points of circles 27, 28 and 29 with the orientation line 37 or the corresponding alignment line 26 now mark target points in such a way that, when the projection point 40 is brought into coincidence with the corresponding target point, the position correction is adjusted, that leads to the correspondingly color-coded continuation trajectory in the corresponding direction.

This is because the continuation trajectories are ascertained on the basis of precisely these position corrections in the slice defined by the target points. Since the location of the markings, here specifically the circles 27, 28 and 29, is known, the resulting position corrections in the slice are also known and the corresponding continuation trajectories may be ascertained in step S4, obviously taking account of the point of application. Herein, the user is intuitively clearly and fully aware of the corresponding directions and their impacts as well as which of the lines 37, 38 is the orientation line 37, since the examination object 19 is accordingly located before the user and the representation also relates to the slice.

As represented in FIGS. 11 and 12, in this first embodiment, the user has selected the continuation trajectory according to the lower graphical element 35 (blue) since this is most likely to lead to the target area and therefore performs position correction at the point of application at the proximal end of the instrument 2 in such a way that, as shown in FIG. 12, the projection point 40 comes to lie on the left-hand intersection of the blue circle 28 with the alignment line 26 that has been brought into coincidence with the orientation line 37. If there is now an advancement, the continuation trajectory represented by the lower graphical element 35 is established. Here, the medical instrument 2 remains in the axial slice represented by the slice image of the image data 32 on which the representation 31 is based, so that no changes are required for further control scans and for the orientation line 37.

Figure 14:
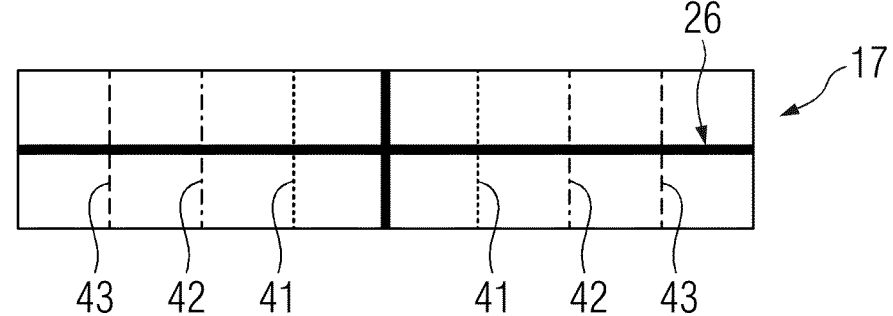
FIG. 14 depicts an alignment element for an embodiment of the first embodiment of FIG. 4.
Figure 15:
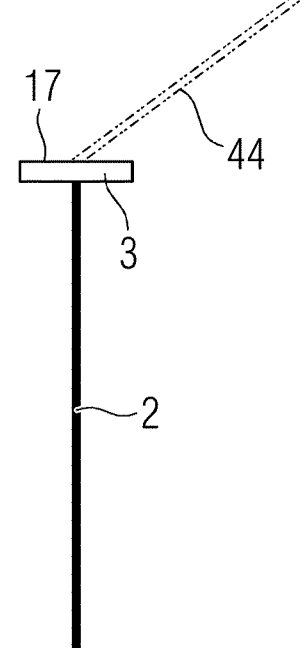
FIG. 15 depicts an illustration of the instruction in a first state of the instrument and alignment element according to an embodiment.
Figure 16:
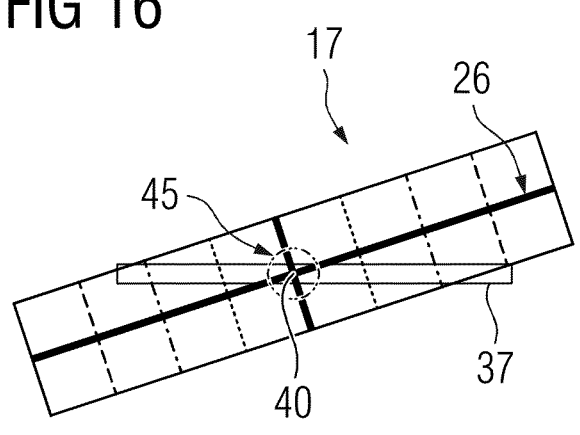
FIG. 16 depicts an illustration of the first state on the projection surface according to an embodiment.

For example if, as represented, work is always to be carried out in a firmly specified slice, it is also possible to use an embodiment of the projection surface 17 of the alignment element 3 as represented for the second embodiment in FIG. 14. Here, the projection surface 17 is held in an elongate manner in the direction of the (here only one) alignment line 26 and the circles 27, 28, 29 are reduced to bars 41 (green), 42 (blue) and 43 (violet) perpendicular to the alignment line 26.

In the second embodiment, by way of example, the adjustment options for the second laser fan 25 or the patient bench 8 are not sufficient for positioning the projection point 40 meaningfully in the center of the projection surface 17, so that, in addition to the orientation line 37, that continues to indicate the representation orientation, i.e., the orientation of the axial slice, the light-guiding facility projects an orientation point 45 onto the projection surface 17 by a laser light source for outputting a laser beam 44 in order to form the light pattern and define the projection point 40. The laser beam 44 and the laser fan 24 may have different colors.

Figure 17:
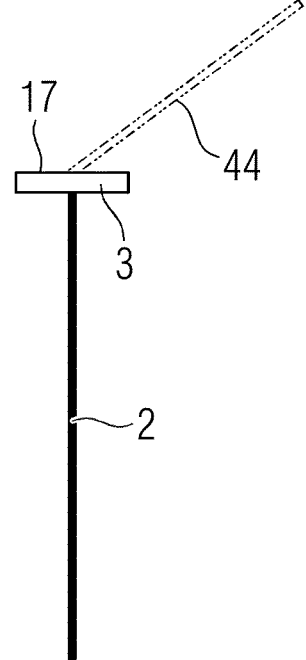
FIG. 17 depicts an illustration of the instruction in a second state of the instrument and alignment element according to an embodiment.
Figure 18:
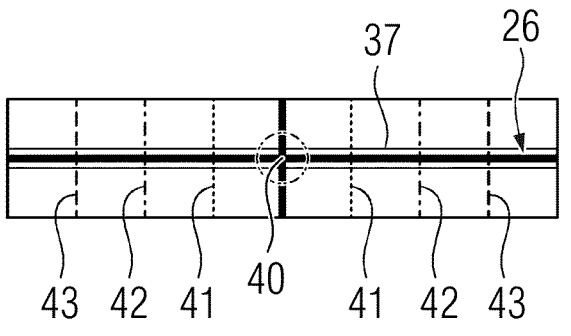
FIG. 18 depicts an illustration of the second state on the projection surface according to an embodiment.

FIGS. 15 and 16 again show the initial state (first situation) in which the orientation line 37 and the alignment line 26 do not coincide, but the projection point 40 already lies on the central crossover point of the markings. In FIGS. 17 and 18 (second situation), the alignment element 3 is rotated such that the orientation line 37 and the alignment line 26 are superimposed. Similarly to FIGS. 9 and 10, the intersection of the bars 41, 42 and 43 with the alignment line 26 now indicate the target points to which the projection point 40 is to be moved to select the continuation trajectory shown accordingly in the representation 31 as graphical element 34, 35 or 36.

Figure 19:
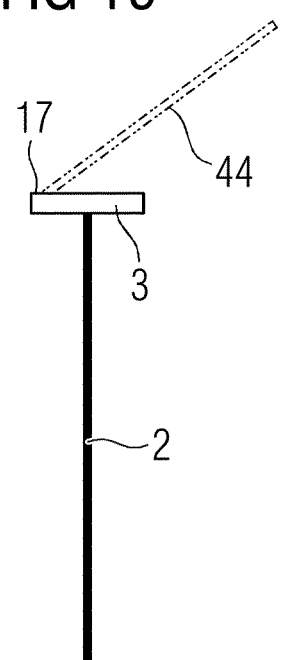
FIG. 19 depicts an illustration of the instruction in a third state of the instrument and alignment element according to an embodiment.
Figure 20:
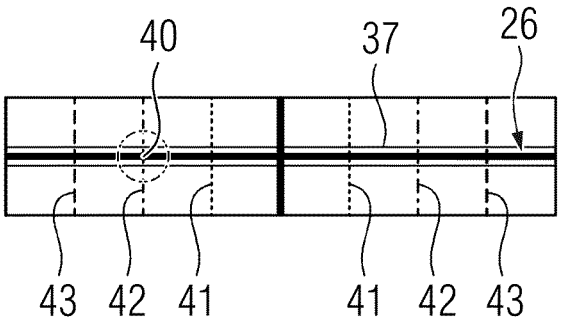
FIG. 20 depicts an illustration of the third state on the projection surface according to an embodiment.

In the third situation, according to FIGS. 19 and 20, the continuation trajectory assigned to the lower graphical element 35 was again selected by corresponding position correction since the projection point 40 is now located on the target point defined by the left-hand bar 42 (blue).

Figure 21:
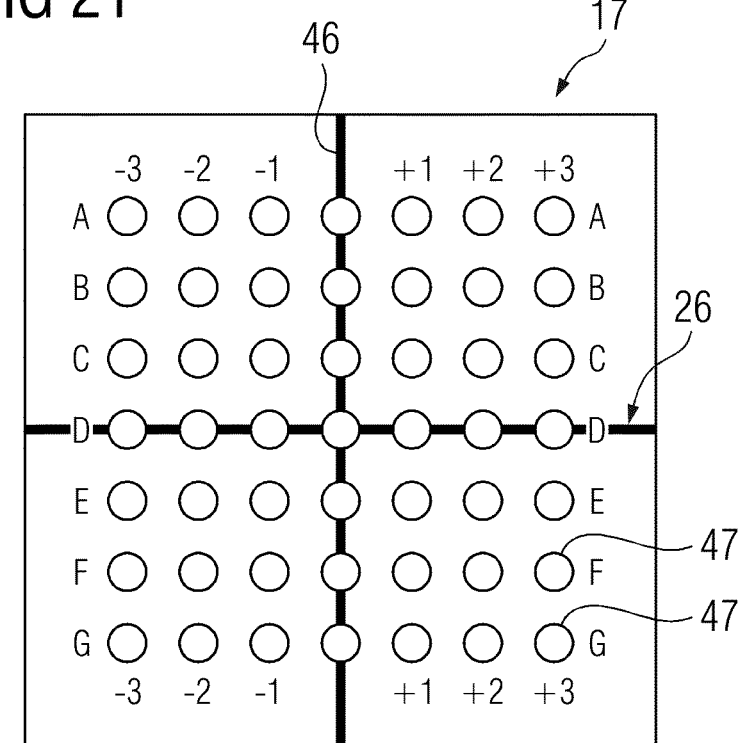
FIG. 21 depicts an alignment element for a third embodiment of the first embodiment.

FIG. 21 depicts a third embodiment for the first embodiment in which, in addition to a cross formed by an alignment line 26 and a further line 46, points 47 are accommodated as matrix-like markings of a coordinate grid with corresponding labels. Here, coordinates of the corresponding points 47 may, for example, be assigned as target points to the graphical elements 34, 35, 36 as marking information in the representation 31. Relative information is also possible if, for example, the projection point 40 cannot be placed at the crossover point of the alignment line 26 with the further line 46.

In the second embodiment, at least one marking indicating an alignment point on the projection surface 17 is sufficient, because, here, the actuating unit 16 actuates the light-guiding facility 7 for marking a projection point assigned to a continuation trajectory on the projection surface 17 in such a way that this projection point is to be brought into congruence with the alignment point in order to select the assigned continuation trajectory, i.e., to adjust the necessary position correction.

Figure 22:
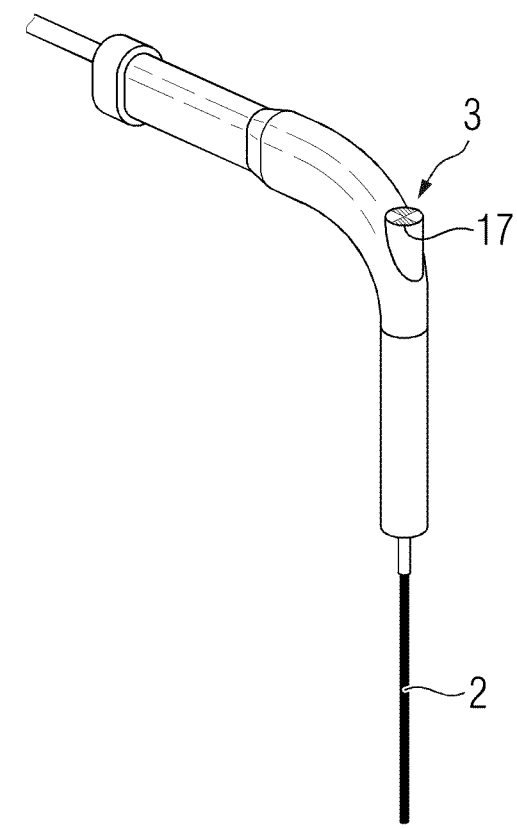
FIG. 22 depicts a partial schematic view of an instrument with an integrated alignment element for the second embodiment.

Since simpler markings may be used in this case, FIG. 22 depicts an embodiment in which the alignment element 3 is integrated in the instrument 2, namely a proximal end surface as a projection surface 17.

Figure 23:
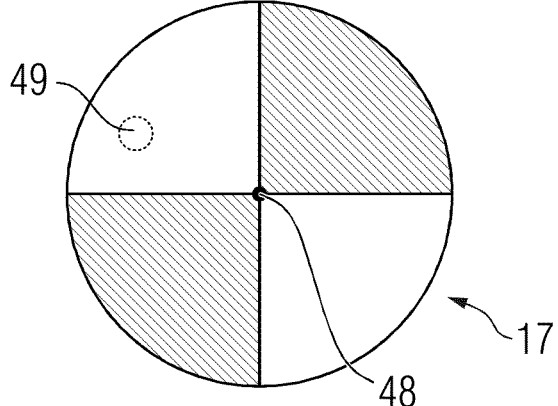
FIG. 23 depicts an illustration to explain an embodiment of the second embodiment.

FIG. 23 depicts this marking more precisely that centrally defines an alignment point 48 (corresponding to the longitudinal direction of at least the proximal portion 21 without position correction). It may be seen that the projection point 49 as the light pattern or part of the light pattern is offset thereto. If the position of the instrument 2 is now corrected at the point of application such that the alignment point 48 and the projection point 49 coincide, the position correction for reaching the continuation trajectory assigned to the projection point 49 has been undertaken and this may be reached by advancement.

In the case of a projection point 49, the marking information in the representation 31 may highlight the assigned continuation trajectory individually, while, in the case of a plurality of projection points 49, an assignment may also be made using distinguishable optical properties.

For example, in an embodiment of the second embodiment in which only one projection point 49 is used, it is useful to use the optional step S6 in order to select the desired continuation trajectory already in the representation 31, for example, and then to have the matching projection point 49 projected for outputting the positioning instruction.

In this context, it is, however, also possible that a continuation trajectory that is optimally suitable for reaching the instrument target is automatically determined or selected and indicated in the representation 31 and a suitable projection point 49 is projected by the guidance facility 7.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A medical intervention device comprising:
an elongate medical instrument configured to be partially inserted into an intervention area of an examination object for an intervention, wherein the elongate medical instrument has a proximal portion to be arranged outside the examination object for manual handling of the elongate medical instrument and is at least partially bendable;

an alignment element arranged on and/or integrated with the elongate medical instrument, wherein the alignment element includes a projection surface with at least one marking that marks at least one point;

a representation facility;

a processing facility comprising:

an evaluation unit configured to ascertain at least one predictive continuation trajectory from image data of the examination object representing the intervention area and positioning data describing a current position and a location of the elongate medical instrument using property data describing a bendability of the elongate medical instrument, and an output unit configured to output a representation of the intervention area and the at least one predictive continuation trajectory based on the image data on the representation facility; and a light-guiding facility comprising a light source configured to emit at least one light pattern onto the projection surface in such a way that a combined view of at least one of the at least one marking and the light pattern produces a positioning instruction for manual position correction at the proximal portion of the elongate medical instrument in order to select the at least one predictive continuation trajectory upon further insertion of the elongate medical instrument.

2. The medical intervention device of claim 1, wherein the light pattern marks a projection point that in order to select the selected at least one predictive continuation trajectory is to be brought into congruence with a marking assigned to the selected at least one predictive continuation trajectory, wherein the output unit is configured to generate the representation with marking information assigned to the at least one predictive continuation trajectory and describing the assigned marking.

3. The medical intervention device of claim 2, wherein the light pattern comprises at least one orientation line indicating an orientation of the representation.

4. The medical intervention device of claim 3, wherein the light pattern for marking the projection point on the at least one orientation line comprises an orientation point that is controllably adjusted by the processing facility on the basis of the positioning data.

5. The medical intervention device of claim 4, wherein the marks have at least one alignment line to be brought into coincidence with the orientation line.

6. The medical intervention device of claim 5, wherein marks that may be assigned to continuation trajectories are provided along the alignment line so that when the alignment line is brought into coincidence with the orientation line for each position correction, the elongate medical instrument remains in a slice marked by the orientation line.

7. The medical intervention device of claim 6, wherein the marks form at least part of a crosshair comprising the at least one alignment line and/or one or more rings, wherein a center of the crosshair coincides with the projection point before the position correction is undertaken, and wherein one or more rings of the crosshair are assigned to respective continuation trajectories, and/or the marks form a coordinate grid, wherein coordinates are assigned at least to markings that may be assigned to the continuation trajectories.

8. The medical intervention device of claim 1, wherein the alignment element has only one marking defining an alignment point and the processing facility is configured to actuate the light-guiding facility for marking a projection point on the projection surface that is assigned to a respective predictive continuation trajectory and that, in order to select the assigned respective predictive continuation trajectory, is to be brought into congruence with the alignment point.

9. The medical intervention device of claim 1, wherein the proximal portion has a point of application for manually undertaking the position correction, wherein the evaluation unit is configured to take account of the location of the point of application when ascertaining the at least one predictive continuation trajectory.

10. The medical intervention device of claim 1, further comprising:

an imaging facility configured for capturing at least part of the image data.

11. The medical intervention device of claim 10, wherein the light-guiding facility is permanently installed on the imaging facility and/or integrated therein.

12. The medical intervention device of claim 1, wherein the evaluation unit is configured to ascertain the positioning data at least partially from the image data and/or to register image data with provided preliminary image data of the examination object.

13. The medical intervention device of claim 1, wherein the evaluation unit is configured to ascertain property data from provided instrument information.

14. The medical intervention device of claim 1, wherein the light source is a laser light source.

15. A computer-implemented method for ascertaining and outputting a positioning instruction for an elongate medical instrument that is configured to be partially inserted into an intervention area of an examination object for an intervention, wherein the elongate medical instrument includes a proximal portion to be arranged outside the examination object for manual handling of the elongate medical instrument and is at least partially bendable, wherein an alignment element arranged on the elongate medical instrument and/or integrated therein, wherein the alignment element includes a projection surface with at least one marking which marks at least one point is used, wherein, with the elongate medical instrument that is already partially inserted into the examination object, the method comprising:

providing image data of the examination object representing the intervention area via an interface of a processing facility and ascertaining positioning data describing a current position and a location of the elongate medical instrument;

using an evaluation unit of the processing facility to ascertain at least one predictive continuation trajectory from the image data and the positioning data using property data describing a bendability of the elongate medical instrument;

outputting a representation of the intervention area and the at least one predictive continuation trajectory based on the image data by an output unit of the processing facility on a representation facility; and operating a light-guiding facility comprising a light source for emitting at least one light pattern onto the projection surface in such a way that a combined view of at least one of the at least one marking and the light pattern produces the positioning instruction for manual position correction at the proximal portion of the elongate medical instrument in order to achieve one to be selected of the at least one predictive continuation trajectory upon further insertion of the elongate medical instrument.

\* \* \* \* \*